United States Patent
Vasselin et al.

(10) Patent No.: US 8,729,306 B2
(45) Date of Patent: May 20, 2014

(54) PROCESS FOR THE PREPARATION OF NITROGEN SUBSTITUTED AMINOTETRALINS DERIVATIVES

(75) Inventors: David Vasselin, Brussels (BE); Nicolas Carly, Brussels (BE); Celal Ates, Brussels (BE)

(73) Assignee: UCB Pharma GmbH, Monheim (DE)

(*) Notice: Subject to any disclaimer, the term of this patent is extended or adjusted under 35 U.S.C. 154(b) by 96 days.

(21) Appl. No.: 13/576,289

(22) PCT Filed: Feb. 3, 2011

(86) PCT No.: PCT/EP2011/051549
§ 371 (c)(1),
(2), (4) Date: Jul. 31, 2012

(87) PCT Pub. No.: WO2011/095539
PCT Pub. Date: Aug. 11, 2011

(65) Prior Publication Data
US 2012/0302790 A1    Nov. 29, 2012

Related U.S. Application Data

(60) Provisional application No. 61/301,741, filed on Feb. 5, 2010.

(51) Int. Cl.
C07C 233/05    (2006.01)
C07C 233/65    (2006.01)
C07C 231/08    (2006.01)
C07C 231/12    (2006.01)

(52) U.S. Cl.
USPC .......................................... 564/222; 564/184

(58) Field of Classification Search
USPC ................................................. 564/184, 222
See application file for complete search history.

(56) References Cited

U.S. PATENT DOCUMENTS 6,271,005 B1    8/2001    Khumtaveeporn et al.

OTHER PUBLICATIONS

Imanishi et al., "Discovery of a Novel Series of Benzoic Acid Derivatives as Potent and Selective beta3 Adrenergic Receptor Agonists with good oral Bioavailability. 3. Phenylethanolaminotetraline (PEAT) Skeleton Containing Biphenyl or Biphenyl Ether Moiety", J. Med. Chem., 2008, vol. 51, 4804-4822.

Sala et al., "Ruthenium-catalyzed asymmetric hydrogenation of N-(3,4-dihydro-2-naphthalenyl)-acetamide", Catalysis Communications, 2008, vol. 9, 117-119.
Renaud et al., "Ruthenium-Catalysed Enantioselective Hydrogenation of Trisubstituted Enamides Derived from 2-Tetralone and 3-Chromanone: Influence of Substitution on the Amide Arm and the Aromatic Ring", Adv. Synth. Catal., 2003, vol. 345, 230-238.
Patureau et al., "Sulfonamido-Phosphoramidite Ligands in Cooperative Dinuclear Hydrogenation Catalysis", J. Am. Chem. Soc., 2009, vol. 131, 6683-6685.
Sandee et al., "Ureaphos: supramolecular bidentate ligands for asymmetric hydrogenation", Chem. Communc., 2007, 864-866.
Zhang et al., "Highly Enantioselective Hydrogenation of Cyclic Enamides Catalyzed by a Rh-PennPhos Catalyst", J. Org. Chem., 1999, vol. 64, 1774-1775.
Jiang et al., "Screening of a Supramolecular Catalyst Library in the Search for Selective Catalysts for the Asymmetric Hydrogenation of a Difficult Enamide Substrate", Angew. Chem. Int. Ed., 2006, vol. 45, 1223-1227.
Selditz U et al., "Impact of Substituents on the Enantioseparation of Racemic 2-Amidotetralins on Polysaccharide Stationary Phases 1. Chiralcel Od", Chirality, 1996, 8(8), 574-578.
Homan et al., "Synthesis and Pharmacology of the Enantiomers of the Potential Atypical Antipsychotic Agents 5-OMe-BPAT and 5-OMe-(2, 6-di-OMe)-BPAT", Bioorganic & Medicinal Chemistry, 1999, vol. 7, 1263-1271.

*Primary Examiner* — Shailendra Kumar
(74) *Attorney, Agent, or Firm* — McDonnell Boehnen Hulbert & Berghoff LLP

(57) ABSTRACT

The present invention provides an alternative synthesis of N-substituted aminotetralines which synthesis comprises catalytic asymmetric hydrogenation of compounds of general formula (A).

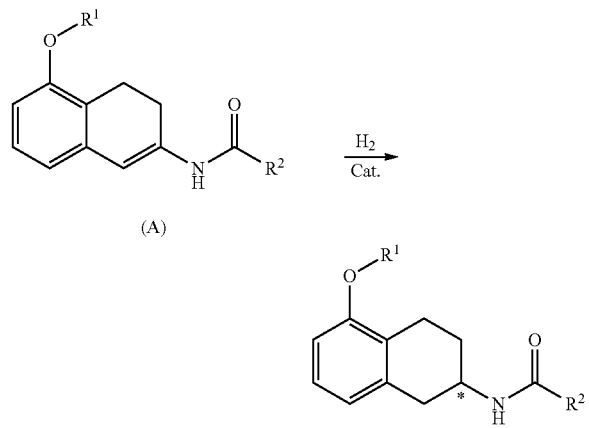

13 Claims, No Drawings

PROCESS FOR THE PREPARATION OF NITROGEN SUBSTITUTED AMINOTETRALINS DERIVATIVES

This application is a U.S. national phase of International Application No. PCT/EP2011/051549 filed on Feb. 3, 2011, which claims priority to U.S. Provisional Application No. 61/301,741 filed on Feb. 5, 2010, the disclosures of which are incorporated herein by reference in their entirety.

The present patent application relates to a novel process for the preparation of nitrogen-substituted aminotetralins.

Particularly, the present patent application relates to a novel process for the preparation of substantially optically pure nitrogen-substituted aminotetralins.

In a particular embodiment, the present application relates to an improved process for the manufacture of rotigotine.

Rotigotine is the International Non-Proprietary Name (INN) of compound (−)-5,6,7,8-tetrahydro-6-[propyl-[2-(2-thienyl)ethyl]amino]-1-naphthalenol having the structure shown below (C1).

(C1)

rotigotine

Rotigotine is a non-ergolinic D1/D2/D3 dopamine agonist that resembles dopamine structurally and has a similar receptor profile but a higher receptor affinity.

In contrast to other non-ergolinic dopamine agonists, Rotigotine has significant D1 activity, which may contribute to a more physiological action.

In contrast to ergolinic compounds, Rotigotine has a very low affinity for 5 HT2B receptors and thus a low risk of inducing fibrosis.

Actions on non-dopaminergic receptors (such as 5-HT1A agonism and A2B antagonism) may contribute to other beneficial effects, such as antidyskinetic activity, neuroprotective activity and antidepressive effects.

Rotigotine is disclosed as active agent for treating patients suffering from Parkinson's disease (described in WO 2002/089777), Parkinson's plus syndrome (described in WO 2005/092331), depression (described in WO 2005/009424) and the restless-legs syndrome (described in WO 2003/092677) as well as for the treatment or prevention of dopaminergic neurone loss (described in WO 2005/063237) and treatment of pain (PCT/EP2007/005381).

International patent application WO 01/38321 describes a process of manufacture of nitrogen substituted aminotetralines and in particular rotigotine.

The present invention provides an alternative process for the manufacture of rotigotine.

In particular, the present invention provides an alternative synthesis of N-substituted aminotetralines.

In a first aspect, the present invention provides a compound of general formula (A), (A)

wherein $R^1$ is alkyl, and $R^2$ is alkyl or phenyl.

The term "alkyl", as used herein, is a group which represents saturated, monovalent hydrocarbon radicals having straight (unbranched) or branched moieties, or combinations thereof, and containing 1-8 carbon atoms, preferably 1-6 carbon atoms; more preferably alkyl groups have 1-4 carbon atoms.

"Alkyl" groups according to the present invention may be unsubstituted or substituted. Preferred alkyl groups are methyl and ethyl.

In a particular embodiment, the first aspect of the present invention provides a compound of formula (A) wherein $R^1$ is a $C_{1-4}$ alkyl and $R^2$ is a $C_{1-4}$ alkyl or a phenyl.

In a further particular embodiment, the first aspect of the present invention provides a compound of formula (A) wherein $R^1$ is $C_{1-4}$ alkyl and $R^2$ is ethyl or phenyl, herein after referred to as (A1).

In a more particular embodiment, compound (A) is N-(5-methoxy-3,4-dihyrdonaphtalen-2-yl)propionamide, herein after referred to as (A2).

(A2)

Compounds of general formula (A) may be synthetized by reacting compounds of general formula (X) wherein $R^1$ is as defined for compound of formula (A) with an amide compound of formula (Y) wherein $R^2$ is as defined for compound of formula (A), according to following scheme 1.

Scheme 1

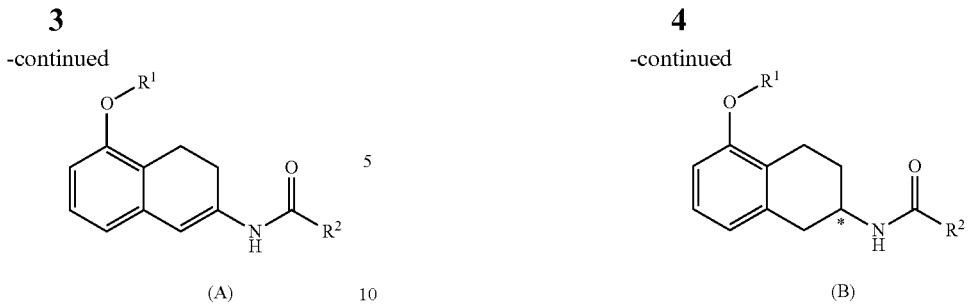

(A)

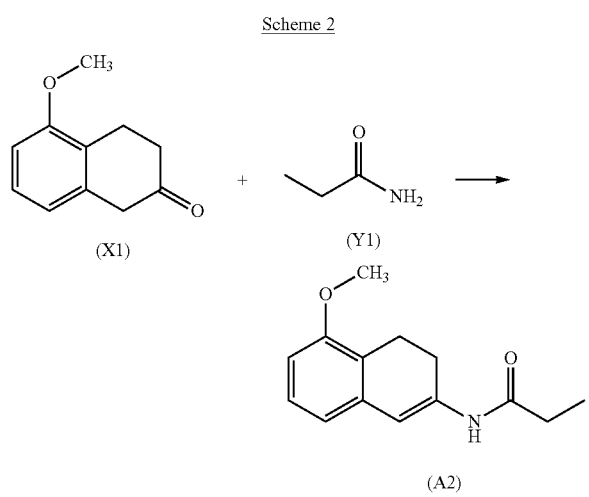

Derivatives of compound of formula (X) wherein the ketone is replaced by a ketal or by an alkyl bisulfite adduct may also be reacted in the same way with compound of formula (Y) to afford compound of formula (A).

In particular compound of formula (A2) may be synthetized by reacting 5-methoxy-2-tetralone (X1), which is commercially available, with propionamide (Y1), in the presence of a dehydrating agent, for example p-toluene sulfonic acid monohydrate, or in the presence of an acid catalyst, according to the following scheme 2.

Scheme 2

Typically, the reaction is performed in a solvent which forms a good azeotrope with water, for example in toluene.

In a second aspect, the present invention relates to the use of compounds of formula (A) as synthetic intermediates.

In particular, the second aspect of the present invention relates to a process of manufacture of compounds of formula (B) wherein $R^1$ and $R^2$ are as defined for compounds of formula (A), which process comprises hydrogenation of compounds of general formula (A), as shown in the following scheme 3.

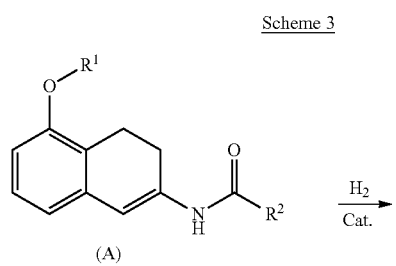

Scheme 3

(B)

In a particular embodiment of said second aspect, the present invention relates to a process of manufacture of compounds of formula (B), wherein $R^1$ and $R^2$ are as defined for compounds of formula (A), which process comprises catalytic asymmetric hydrogenation of compound of formula (A).

Catalytic asymmetric hydrogenation is described in a great number of books and publications readily available to the man skilled in the art. An example of review article on catalytic asymmetric hydrogenation is William S. Knowles, *Angew. Chem. Int. Ed.*, 2002, 41, 1998-2007.

Hitherto, there have been numerous attempts in the art towards an enantiomeric selective catalyst system for effecting stoichiometric efficient asymmetric hydrogenation of enamides. Asymetric hydrogenation of some tetralone based enamides are described in international patent application WO 99/18065 filed by CHIROTECH.

Catalytic asymmetric hydrogenation according to the present invention is generally performed in the presence of a chiral catalyst.

The chiral catalyst according to the present invention is generally based on rhodium (I) or ruthenium (II).

In one embodiment, the chiral catalyst according to the present invention is based on ruthenium (II) complexed by a chiral chelating agent.

There is a great number of chiral chelating agents available commercially or described in the literature. Generally, the chiral chelating agent according to the present invention comprises a phosphine ligand.

(Bis)Phosphine ligands are often difficult to prepare because they possess two chiral centers, which adds to their cost. Furthermore, asymmetric hydrogenation requires the use of special equipment capable of handling $H_2$, which adds to capital costs.

Therefore there is a need to develop a process which make the large scale production of aminotetralins eco-friendly, safe and yet economically feasible. Present invention bridges this gap and discloses the novel process, which is environmental friendly as well as eliminates the use of costly chiral ligands or auxiliary, column chromatography and suitable for industrial scale up.

A number of catalysts for catalytic asymmetric hydrogenation comprising phosphine ligands have been described in the literature. An example of review article dedicated to chiral phosphorus ligands is W. Tang & X. Zhang, *Chem. Rev.* 2003, 103, 3029-3069. It has further been observed on an industrial scale that the catalyst systems frequently tend to become deactivated depending on the catalyst precursor, the substrate and the ligands. It has further been found that not all catalyst systems that are known in the art enable a complete conversion of the starting materials into the target product with a high enantiomeric selectivity. Thus, there is a continuous need in the art for a process that enables an enantioselective hydrogenation of imines with a high conversion as well as a high enantiomeric excess of the target product wherein the catalyst system is cost effective.

Although a lot of information on catalytic asymmetric hydrogenation is available in the art, finding, for a given substrate, the appropriate catalyst and reaction conditions to obtain the desired product with a high enantioselectivity requires a great amount of experimental work. Furtheron, despite the inherent advantages in using asymmetric catalysis to produce single-enantiomer molecules, the process is not readily amenable to use at an industrial scale because of a number of factors: such as the ready availability of the chiral catalyst for public or licensed use in the required quantity at an affordable price, the presence of impurities in the catalyst, which can either inhibit the effectiveness of the catalyst itself or get carried into the final product where they are difficult to remove and that, there is no single ligand family, much less an individual member of a family, which leads to high enantiomer selectivity with all substrates.

Examples of phosphine ligands which may be used according to the present invention are (S)-2,2'-bis(diphenylphosphino)-1,1'-binaphthyl ((S)-BINAP), (−)-1,2-Bis((2R,5R)-2,5-dimethylphospholano)benzene ((R,R)-Me-DuPhos), (3S,3'S,4S,4'S,11bS,11'bS)-(+)-4,4'-Di-t-butyl-4,4',5,5'-tetrahydro-3,3'-bi-3H-dinaphtho[2,1-c:1',2'-e]phosphepin ((S)-BINAPINE), (−)-1,2-Bis(2R,5R)-2,5-diphenylphospholano)ethane ((R,R)-Ph-BPE), (R)-(+)-5,5'-Bis(diphenylphosphino)-4,4'-bi-1,3-benzodioxole (SEGPHOS), [4(R)-(4,4'-bi-1,3-benzodioxole)-5,5'-diyl]bis[diphenylphosphine], (R,R)-1,2-Bis[(R)-4,5-dihydro-3H-binaphtho(1,2-c:2',1'-e)phosphepino]benzene (BINAPHANE), (R)-1,13-Bis(diphenylphosphino)-7,8-dihydro-6H-dibenzo[f,h][1,5]dioxonin (TUNEPHOS), (1S,1S',2R,2R')-(+)-1,1'-Di-tert-butyl-[2,2]-diphospholane (TANGPHOS), R-(2-methoxyphenyl)-[2-[(2-methoxyphenyl)-phenylphosphanyl]ethyl]-phenylphosphane (DIPAMP).

In a particular embodiment according to the present invention, the chiral chelating agent comprises substantially optically pure phosphine ligands, i.e. phosphine ligands in which at least about 95%, preferably at least about 96%, more preferably at least about 97%, most preferably at least about 98%, even most preferably at least about 99% of the compound has the stereogenic center or stereogenic centres in a given configuration (R) or (S).

In a particular embodiment according to said invention, said stereogenic centre has a (R)-configuration.

Generally the phosphine ligand forms a complex with the metal, e.g. ruthenium (II) and is associated to a counterion or to an olefin. Said complex acts as the catalyst to perform the reaction.

Examples of counterions which may be associated to the complex according to the present invention are halide (halogen(−)), BPh$_4$(−), ClO$_4$(−), BF$_4$(−), PF$_6$(−), PCl$_6$(−), acetate (COO(−)), triflate (OTf(−)), mesylate and tosylate.

Examples of olefins that may be associated to the complex according to the present invention are ethylene, 1,3-butadiene, benzene, cyclohexadiene, norbornadiene and cycloocta-1,5-diene.

The catalyst resulting from the association of the metal, phosphine ligand and associated counterion and/or olefin may be pre-formed or generated in situ in the reaction media.

Examples of catalysts according to the present invention which may be pre-formed or generated in situ are (R)-(+)-(2,2'-Bis(diphenylphosphino)-1,1'-binaphthyl)ruthenium, (−)-1,2-Bis((2R,5R)-2,5-dimethylphospholano)benzene(1,5-cyclooctadiene)rhodium(I) tetrafluoroborate, (3S,3'S,4S,4'S,11bS,11'bS)-(+)-4,4'-Di-t-butyl-4,4',5,5'-tetrahydro-3,3'-bi-3H-dinaphthpo[2,1-c:1',2'-e]phosphepin(1,5-cyclooctadiene) rhodium (I) tetrafluoroborate, (−)-1,2-Bis(2R,5R)-2,5-diphenylphospholano)ethane(1,5-cyclooctadiene)rhodium (I) tetrafluoroborate and chloro[(R)-(+)-5,5'-bis(diphenylphosphino)-4,4'-bi-1,3-benzodioxole](p-cymene)ruthenium(II) chloride.

Said catalytic asymmetric hydrogenation is generally performed in the presence of a solvent. Examples of solvents according to the present invention are methanol and mixtures of methanol with another solvent such as dichloromethane.

Said catalytic asymmetric hydrogenation is generally performed at a temperature lower than about 100° C. In one embodiment said hydrogenation is performed at temperature greater than about 20° C. For example, said catalytic asymmetric hydrogenation may be performed at a temperature of about 60° C.

Said catalytic asymmetric hydrogenation is generally performed under pressure of hydrogen in an appropriate vessel. Generally, the pressure of hydrogen is comprised between about 2 barg and about 50 barg.

"Barg" as herein defined represents the unity for the measured pressure with reference to atmospheric pressure i.e. pressure (Barg)=measure pressure (Bar)-atmospheric pressure (Bar).

The process according to the present invention comprising catalytic asymmetric hydrogenation of compounds of formula (A) generally provides optically enriched compounds of formula (B).

In a preferred embodiment said process comprising catalytic asymmetric hydrogenation of compounds of formula (A) in the presence of chiral catalyst provides substantially optically pure compounds of formula (B).

The term "substantially optically pure" as used herein when referring to a particular compound means that at least about 95%, preferably at least about 96%, more preferably at least about 97%, most preferably at least about 98%, even most preferably at least about 99% of the compound has the stereogenic center indicated by (*) in a given configuration (R) or (S).

Preferably, the process according to said second aspect of the present invention relates to the manufacture of compounds of formula (B) wherein $R^1$ is a $C_{1-4}$ alkyl and $R^2$ is ethyl or phenyl, herein after referred to as compound of formula (B1).

Generally, the catalytic asymmetric hydrogenation according to the present invention provides compounds of formula (B) and (B1) in conversion rates that are greater than about 90%, preferably greater than about 95%, more preferably greater than about 99%.

In a particular embodiment, the present invention relates to a process of manufacture of optically enriched N-(5-methoxy-1,2,3,4-tetrahydronaphtalen-2-yl)-(S)-propionamide comprising catalytic asymmetric hydrogenation of N-(5-methoxy-3,4-dihydronaphtalen-2-yl)propionamide.

The expression "optically enriched N-(5-methoxy-1,2,3,4-tetrahydronaphtalen-2-yl)-(S)-propionamide" means that more than about 50%, preferably more than about 75%, more preferably more than about 85%, most preferably more than about 94% of the compound has the stereogenic center indicated by (*) in configuration (S).

In a further particular embodiment the present invention relates to a process of manufacture of substantially optically pure N-(5-methoxy-1,2,3,4-tetrahydronaphtalen-2-yl)-(S)-propionamide, herein after referred to as (B2), which process comprises catalytic asymmetric hydrogenation of N-(5-methoxy-3,4-dihydronaphtalen-2-yl)propionamide (A2), as shown in following scheme 4.

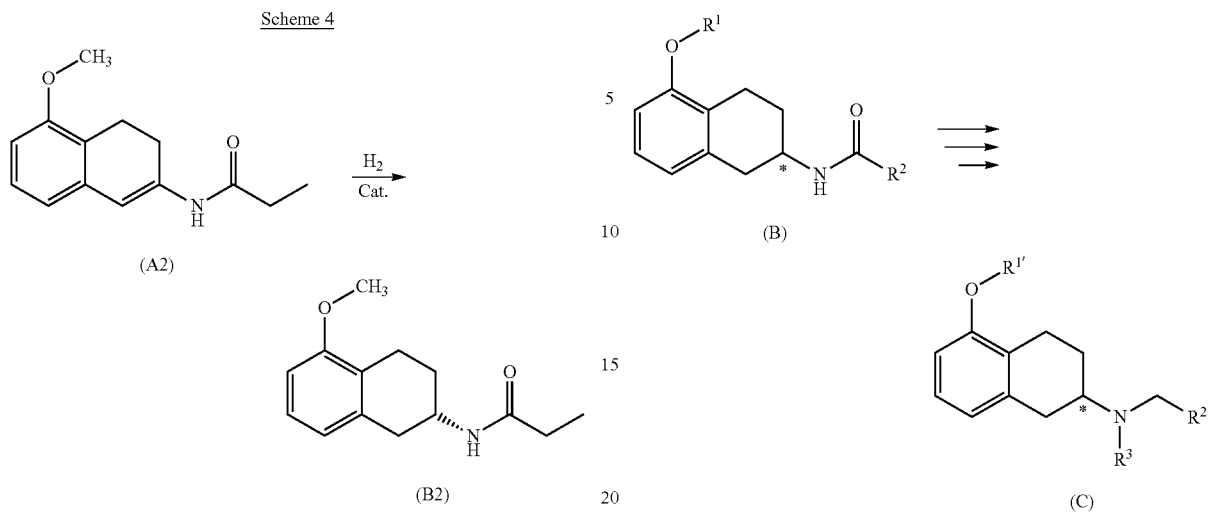

The expression "substantially optically pure N-(5-methoxy-1,2,3,4-tetrahydronaphtalen-2-yl)-(S)-propionamide" means that at least about 95%, preferably at least about 96%, more preferably at least about 97%, most preferably at least about 98%, even most preferably at least about 99% of the compound has the stereogenic center indicated by (*) in configuration (S).

In a particular embodiment according to the present invention the desired enantiomer of (B) is obtained with an enantiomeric excess of at least about 90%, preferably of at least about 94%, more preferably of at least about 98%.

The term "enantiomeric excess" as used herein refers to the amount of an enantiomer with respect to another. It can be calculated as follows:

% ee=[([A]−[B]):([A]+[B])]×100, where [A] is the concentration of one of the enantiomers, and [B] is the concentration of the other enantiomer. In a completely resolved material, the enantiomeric excess is equal in weight to the total material so that % ee is 100%. In this case the optical purity of the compound will be 100%. The concentration of each of the enantiomers is, of course, expressed on the same basis, and can be expressed on either a weight of molar basis because the enantiomers have the same molecular weight.

In a particular embodiment according to the present invention, the process of manufacture of substantially optically pure compound of formula (B2) comprises catalytic asymmetric hydrogenation of N-(5-methoxy-3,4-dihydronaphtalen-2-yl)propionamide (A2), in the presence of hydrogen at a pressure comprised between 2 and 50 bars in methanol and using (R)-(+)-(2,2'-Bis(diphenylphosphino)-1,1'-binaphthyl) ruthenium as chiral catalyst.

Enantiomeric excess of compounds of formula (B), in particular of optically enriched or substantially optically pure compounds of formula (B2), may be further increased by recrystallization of compound of formula (B), (B1) or (B2) in a solvent. Said recrystallization may be iterated if necessary until compound of formula (B), (B1) or (B2) is obtained in the desired optical purity.

Compounds of formula (B) may be further transformed into N-substituted aminotetralines of formula (C), wherein R$^{1'}$ is hydrogen, R$^2$ is as defined for compounds of formula (A) and (B) and wherein R$^3$ is an thienylalkyl group, as shown in following scheme 5.

The "thienylalkyl group" as herein defined represents a group of formula (CH$_2$)n-thienyl wherein, n is an integer comprised between 1 and 3 and thienyl is 2-thienyl or 3-thienyl.

In a particular embodiment according to the present invention, n is 2 and the thienyl is 2-thienyl.

The transformation of (B) into (C) may be performed according to methods described in the literature or known to the man skilled in the art.

In a particular aspect, the present invention relates to a process of manufacture of 5,6,7,8-tetrahydro-6-[propyl-[2-(2-thienyl)ethyl]-amino]-1-naphthalenol (C1), rotigotine, using substantially optically pure N-(5-methoxy-1,2,3,4-tetrahydronaphtalen-2-yl)-(S)-propionamide (B2) obtained as shown in scheme 4 by catalytic asymmetric hydrogenation of N-(5-methoxy-3,4-dihydronaphtalen-2-yl)propionamide (A2), as shown in following scheme 6.

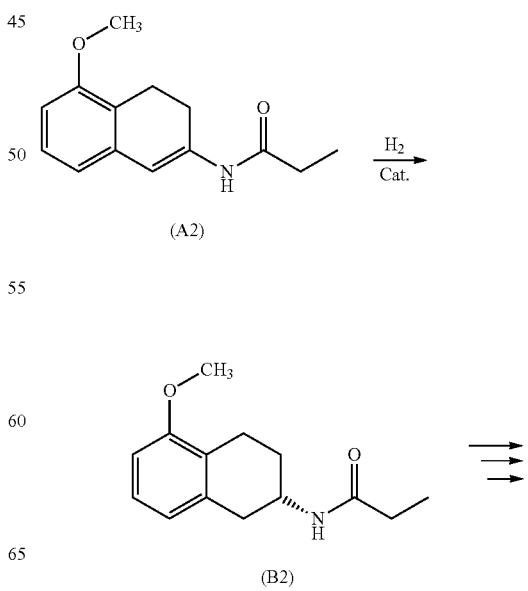

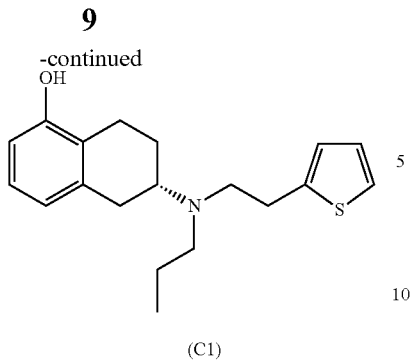

(C1)

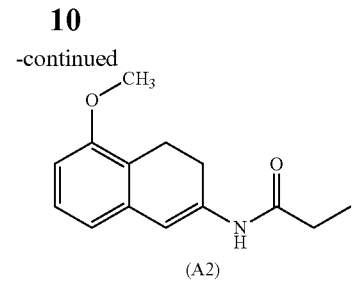

(A2)

EXAMPLES

1HNMR spectra were measured on a Varian 400 MHz and 300 MHz and Varian 400 MHz spectrometer in deuterosolvents with TMS as an internal standard at room temperature.

$^1$H NMR data were reported in the order of chemical shift, multiplicity (s, singlet; d, doublet; t, triplet; q, quartet; m, multiplet; app, apparent and/or multiple resonance), coupling constant (J) in hertz (Hz) and number of protons.

High Performance Liquid Chromatography (HPLC) spectra for enamide formation are recorded on an on an Alliance Waters 2695 equiped with an XBridge 3.5 microns column (4.6×50 mm), detecting with MaxPlot detection (190-350 nm)—starting solvent composition=water:80% vol/water+10% Acetonitrile+10% 100 mM NH4HCO3:10% vol; final solvent composition=0% water+10% 100 mM NH4HCO3:90% vol/acetonitrile:90% vol in 3.3 minutes with plateau to 5 mins followed by re-equilibration period of 1 min to the initial solvent composition. Flow Rate 3 mL/min.

Chiral HPLC are recorded on a Alliance Waters 2695 equipped with a Chiralpak AD-H® 5 μm (250×4.6 mm) column with detection at 229 nm. Eluent is a 95:5 mixture of A=isohexane and B=ethanol/methanol.diethylamine 60/40/02% v/v with a flow of 1 ml/min.

Mass spectra were recorded on waters 3100 triple quadrapole spectrometer. IR spectra were recorded with a Nicolet 380 FT-IR (neat for liquids and KBr pellets for solids).

HPLC was analyzed on different systems Waters 2695 PDA, Agilent 1100 UV, Shimadzu-SCL-10AVP.

The HPLC data were reported in area %.

Melting point was recorded on Polmon moeld No. MP96.

Example 1

Preparation of N-(5-methoxy-3,4-dihydronaphtalen-2-yl)propionamide (A2)

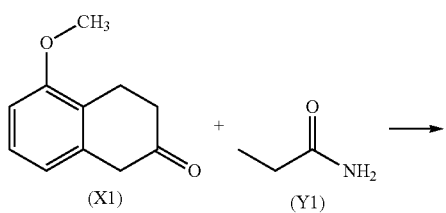

Method A

To a stirred solution of 5-methoxy-2-tetralone (X1) (25.0 g, 0.142 mol) in toluene (500 mL), p-toluenesulfonic acid (2.67 g, 0.014 mmol) and propionamide (25.95 g, 0.355 mmol) were added and the reaction mass was stirred at reflux for overnight using Dean-Stark apparatus. Reaction mass was cooled to room temperature and filtered. Then the organic layer was washed with sodium bicarbonate solution and brine. The organic layer was concentrated and purified by column chromatography (20% ethyl acetate in hexane as eluant 100-200 mesh silica gel).

Compound obtained was dissolved in ethyl acetate (4-vol) at 65° C., and then the solution was cooled to room temperature and kept for 15 h (overnight). The formed solid was filtered and washed with n-hexane and dried in the oven at 50° C. Wt-10.4 g HPLC: 97.01% area, Run Time 30 mins, Column XBridge 3.5 microns column (4.6×150 mm), detecting at 210 nm); solvent A: 0.05% HClO4 solvent B: Acetonitrile. Gradient profile: time/% B: 0.01/0, 19/100, 25.0/100, 25.1/0, 30/0

$^1$H NMR (DMSO-d6): 9.20 (1H, m, ArH), 7.02-7.07 (2H, m, ArH, C=CH), 6.70-6.72 (1H, m, ArH), 6.56-6.58 (1H, m, ArH), 3.75 (3H, s, OMe), 2.69-2.74 (2H, t, CH$_2$), 2.21-2.37 (4H, m, 2×CH$_2$), 1.01-1.06 (3H, t, CH$_3$),

MS (ES+) 232 (M+1) IR (cm−1). 3458, 3274, 3171, 3063, 2954, 2887, 2834, 2358, 1665, 1546, 1461, 1356, 1323, 1267, 1223.

Method B

A solution of 5-Methoxy-2-tetralone (X1) (150 g) in toluene (1000 mL) was prepared in a 2 L jacketed vessel equipped with a Dean-Stark condenser. To this solution was added propylamide (Y1) (150 g) and para-toluenesulfonic acid monohydrate (15 g). The mixture was refluxed for 24 hrs and reaction completion evaluated by hplc. The solution was cooled to 60° C. and 1% w/w Na$_2$CO$_3$ added (450 mL). In order to prevent product precipitation a further 300 mL of toluene was added. The phases were separated and the organic layer washed with water (450 mL). The organic layer was then cooled to 50° C. and aged to allow the product to crystallise. After crystallisation the slurry was further cooled to 5-10° C. and filtered. The filter cake was washed with toluene (2×150 mL), petroleum ether (150 mL) and the white crystalline needles were dried under vacuum at 25° C. to a constant weight of 124.4 g corresponding to compound (A2) (63.2% yield).

Melting point: 147-149° C., $^1$H NMR (CDCl$_3$): 7.13 (1H, m, ArH), 7.09 (1H, m, ArH), 6.69 (2H, m, ArH C=CH), 6.53 (1H, br s, NHCOEt), 3.82 (3H, s, OMe), 2.89 (2H, t, CH$_2$), 2.41 (2H, t, CH$_2$), 2.32 (2H, q, CH$_2$), 1.21 (3H, t, CH$_3$)

Example 2

Preparation of N-substantially optically pure N-(5-methoxy-1,2,3,4-tetrahydronaphtalen-2-yl)-(S)-propionamide (B2) by asymmetric hydrogenation of N-(5-methoxy-3,4-dihydronaphtalen-2-yl)propionamide (A2)

Catalyst: Chloro[(R)-(+)-5,5'-bis(diphenylphosphino)-4,4'-bi-1,3-benzodioxole](p-cymene)ruthenium(II) chloride (R)-SEGPHOS Hydrogenation was carried out using a 300 mL Parr reactor (in hastelloy)

In a glove box, the substrate N-(5-methoxy-3,4-dihydro naphthalen-2-yl)propionamide (A2) (20 g), catalyst (10 mg,) and methanol (100 mL) were loaded in the Parr reactor which was then closed and isolated.

The Parr reactor is then connected to the gas feed. A first pressurization is made with Nitrogen gas (around 50 barg) to make sure that there is no leak. After having released the pressure, a first pressurization is made with Hydrogen gas ($H_2$) at desired pressure (50 barg), the pressure is then released. This cycle of pressurization and pressure released is repeated 3 times.

With the last pressurization, the stirring is started (1000 rpm) and the mixture is heated to a temperature of 60° C. The heating is regulated with the mass temperature of the reaction mass.

After 20 hours of reaction, the $H_2$ pressure is released and the Parr reactor is purged with N2 and the samples are collected.

Conversion of (A2) into (B2) is followed by HPLC and is 100%.

(A2) is obtained with an 84% e.e.

A similar reaction may be performefd by replacing the chloro[(R)-(+)-5,5'-bis(diphenylphosphino)-4,4'-bi-1,3-benzodioxole](p-cymene)ruthenium(II) chloride catalyst (R-SEGPHOS) by Chloro[(R)-(+)-5,5'-bis(diphenylphosphino)-4,4'-bi-1,3-benzodioxole](p-cymene)ruthenium(II) chloride (R-BINAP).

In these conditions, the hydrogenation reaction delivered 100% conversion with an e.e of 81.4%. The reaction solution was evaporated to dryness in vacuo and a 2.00 g sample was crystallised in 14 mL of Acetonitrile/Water (1:1) filtering at room temperature (20-25° C.). The filter cake was washed with 2×4 mL of fresh Acetonitrile/Water (1:1) and dried under vacuum at 50° C. to obtain. 1.19 g of solid. e.e 95.86%.

$^1$H NMR (CDCl$_3$):7.11 (1H, t, ArH), 6.69 (2H, m, ArH), 5.48 (1H, br s, CONH), 4.29 (1H, m, CH), 3.82 (3H, s, OMe), 3.07-3.13 and 2.60-2.66 (2×1H, m, CH$_2$), 2.76 (2H, m, CH$_2$), 2.17 (2H, q, CH$_2$), 2.00 and 1.78 (2×1H, m, CH$_2$) and 1.14 (3H, t, CH$_3$)

The invention claimed is:

1. A compound of general formula (A),

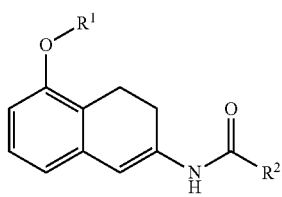

(A)

wherein
$R^1$ is alkyl, and
$R^2$ is alkyl or phenyl.

2. The compound of general formula (A) according to claim 1 wherein $R^1$ is methyl and $R^2$ is ethyl.

3. A process of manufacture of N-substituted amino tetralines of formula (B),

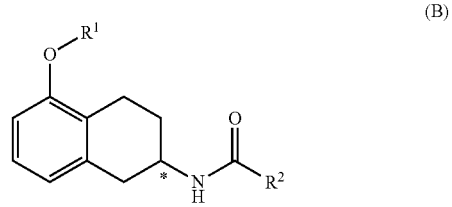

(B)

comprising catalytic asymmetric hydrogenation of compound of formula (A)

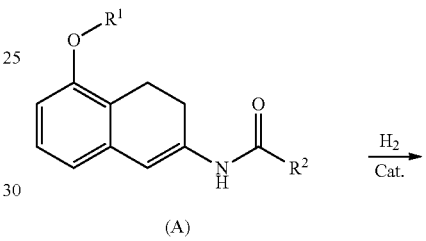

(A)

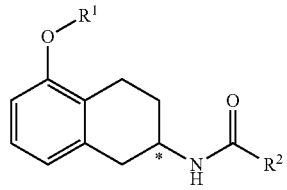

(B)

in the presence of a chiral catalyst.

4. The process according to claim 3 wherein the chiral catalysts is based on ruthenium (II) complexed by a chiral chelating agent.

5. The process according to claim 4 wherein the chiral chelating agent is selected from the group consisting of (S)-2,2'-bis(diphenylphosphino)-1,1'-binaphthyl ((S)-BINAP), (−)-1,2-Bis((2R,5R)-2,5-dimethylphospholano)benzene(1,5-cyclooctadiene)((R,R)-Me-DuPhos), (3S,3'S,4S,4'S,11bS,11'bS)-(+)-4,4'-Di-t-butyl-4,4',5,5'-tetrahydro-3,3'-bi-3H-dinaphtho[2,1-c:1',2'-e]phosphepin(1,5-cyclooctadiene) ((S)-BINAPINE), (−)-1,2-Bis(2R,5R)-2,5-diphenylphospholano) ethane(1,5-cyclooctadiene)((R,R)-Ph-BPE), (R)-(+)-5 ,5'-Bis(diphenylphosphino)-4,4'-bi-1,3-benzodioxole (SEGPHOS), [4(R)-(4,4'-bi-1,3-benzodioxole)-5,5'-diyl]bis [diphenylphosphine], (R,R)-1,2-Bis[(R)-4,5-dihydro-3H-binaphtho(1,2-c:2',1'-e)phosphepino]benzene (BINAPHANE), (R)-1,13-Bis(diphenylphosphino)-7,8-dihydro-6H-dibenzo[f,h][1,5]dioxonin(TUNEPHOS), (1S,1S',2R,2R')-1,1'-Di-tert-butyl-(2,2')-diphospholane (TANGPHOS), (R,R)-Ethylenebis[(2-methoxyphenyl) phenylphosphine], [(1R,2R)-(−)-Bis[(2-methoxyphenyl) phenylphosphino]ethane], (R,R)-1,2-Ethanediylbis[(2-methoxyphenyl)phenylphosphine] and (R,R)-1,2-Bis[(2-methoxyphenyl)(phenylphosphino)]ethane (DIPAMP).

6. The process according to claim 3 wherein the chiral catalyst is selected from the group consisting essentially of (R)-(+)-(2,2'-Bis(diphenylphosphino)-1,1'-binaphthyl)ruthenium, (−)-1,2-Bis((2R,5R)-2,5-dimethylphospholano)benzene(1,5-cyclooctadiene)rhodium(I) tetrafluoroborate, (3S,3'S,4S,4'S,11bS,11'bS)-(+)-4,4'-Di-t-butyl-4,4',5,5'-tetrahydro-3,3'-bi-3H-dinaphtho[2,1-c:1',2'-e]phosphepin(1,5-cyclooctadiene)rhodium(I) tetrafluoroborate, (−)-1,2-Bis(2R,5R)-2,5-diphenylphospholano)ethane(1,5-cyclooctadiene)rhodium(I) tetrafluoroborate and chloro[(R)-(+)-5,5'-bis(diphenylphosphino)-4,4'-bi-1,3-benzodioxole](p-cymene)ruthenium(II) chloride.

7. The process according to claim 3 which is performed in methanol.

8. The process according to claim 3 which is performed at a pressure comprised between about 2 and about 50 barg.

9. The process according to claim 3 which is performed at a temperature lower than about 100° C.

10. The process according to claim 3 wherein compound of formula (A) is obtained by reaction of compound of compound of formula (X1) with compound of formula (Y1) according to the following scheme 1

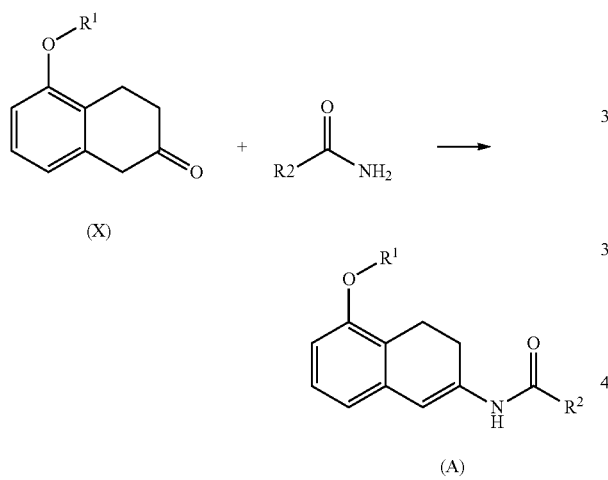

11. A process of manufacture of substantially optically pure N-(5-methoxy-1,2,3,4-tetrahydronaphtalen-2-yl)-(S)-propionamide (B2) comprising catalytic asymmetric hydrogenation of N-(5-methoxy-3,4-dihydronaphtalen-2-yl)propionamide (A2), in the presence of hydrogen at a pressure comprised between 2 and 50 barg in methanol and using a catalyst selected from the group consisting essentially of (R)-(+)-(2,2'-Bis(diphenylphosphino)-1,1'-binaphthyl)ruthenium, (−)-1,2-Bis((2R,5R)-2,5-dimethylphospholano)benzene(1,5-cyclooctadiene)rhodium(I) tetrafluoroborate, (3S,3'S,4S,4'S,11bS,11'bS)-(+)-4,4'-Di-t-butyl-4,4',5,5'-tetrahydro-3,3'-bi-3H-dinaphtho[2,1-c:1',2'-e]phosphepin(1,5-cyclooctadiene)rhodium (I) tetrafluoroborate, (−)-1,2-Bis(2R,5R)-2,5-diphenylphospholano)ethane(1,5-cyclooctadiene)rhodium(I) tetrafluoroborate and chloro[(R)-(+)-5,5'-bis(diphenylphosphino)-4,4'-bi-1,3-benzodioxole](p-cymene)ruthenium(II) chloride

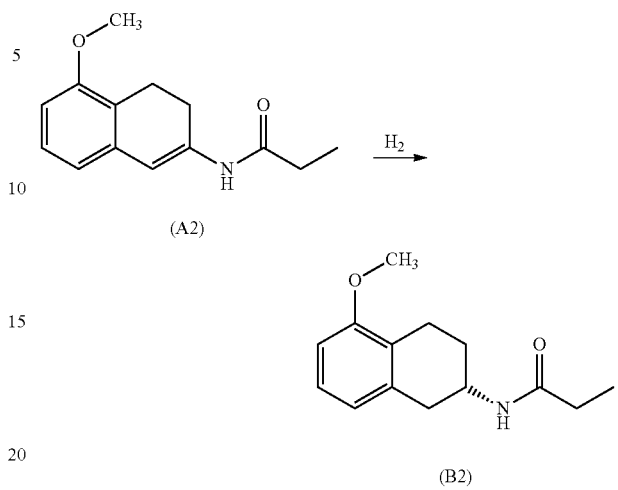

12. The process of manufacture of substantially optically pure N-(5-methoxy-1,2,3,4-tetrahydronaphtalen-2-yl)-(S)-propionamide (B2) according to claim 11 wherein compound of formula (A2) is obtained by reacting 5-methoxy-2-tetralone (X1) with propionamide (Y1), as shown in scheme 2, in the presence of a dehydrating agent or acid catalyst and in a solvent which forms a good azeotrope with water

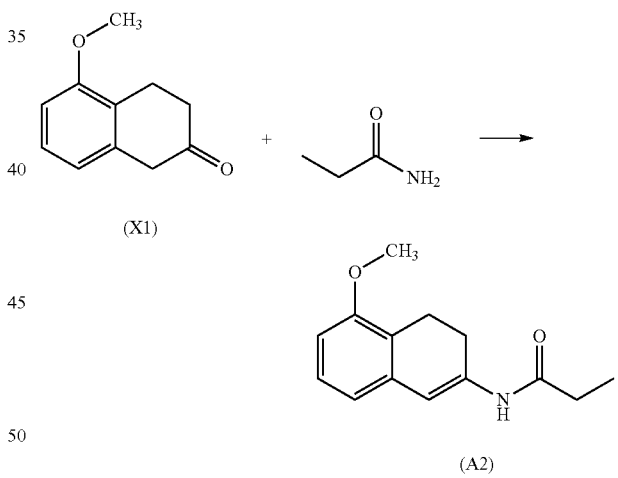

13. A method for the synthesis of 5,6,7,8-tetrahydro-6-[propyl-[2-(2-thienyl)ethyl]-amino]1-naphthalenol (C1) which comprises the step of a catalytic asymmetric hydrogenation of N-(5-methoxy-3,4-dihydronaphtalen-2-yl)propionamide (A2) according to claim 11, to provide N-(5-methoxy-1,2,3,4tetrahydronaphtalen-2-yl)-(S)-propionamide (B2).

* * * * *